(12) United States Patent
Kong et al.

(10) Patent No.: US 10,162,707 B2
(45) Date of Patent: Dec. 25, 2018

(54) OPERATING METHOD FOR APPLICATION PROGRAM AND ELECTRONIC DEVICE SUPPORTING THE SAME

(71) Applicant: Samsung Electronics Co., Ltd, Gyeonggi-do (KR)

(72) Inventors: Ji Young Kong, Gyeonggi-do (KR); Heum Mo Gu, Anyang-si (KR); Sang Mi Kim, Gyeonggi-do (KR); Jeong Yun Kim, Seoul (KR); Kyung Sub Min, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 167 days.

(21) Appl. No.: 15/192,983

(22) Filed: Jun. 24, 2016

(65) Prior Publication Data

US 2016/0378608 A1   Dec. 29, 2016

(30) Foreign Application Priority Data

Jun. 24, 2015   (KR) ........................ 10-2015-0089769

(51) Int. Cl.
*G06F 11/00* (2006.01)
*G06F 11/14* (2006.01)
(Continued)

(52) U.S. Cl.
CPC ...... *G06F 11/1438* (2013.01); *A61B 5/02055* (2013.01); *A61B 5/0402* (2013.01);
(Continued)

(58) Field of Classification Search
CPC ............. G06F 11/1438; G06F 11/1441; G06F 11/1402; G06F 11/1446; G06F 11/1471;
(Continued)

(56) References Cited

U.S. PATENT DOCUMENTS

| 8,959,402 B2* | 2/2015 | Giddi ................. G06F 11/0742 714/47.2 |
| 2004/0261075 A1 | 12/2004 | Yang |

(Continued)

FOREIGN PATENT DOCUMENTS

EP   3043334 A1   7/2016

OTHER PUBLICATIONS

The International Searching Authority, "Notification of Transmittal of the International Search Report and the Written Opinion of the International Searching Authority, or the Declaration, and Written Opinion of the International Searching Authority" International Application No. PCT/KR2016/006726, Sep. 27, 2016, 12 pages, publisher the ISA/KR, International Application Division, Korean Intellectual Property Office, Daejeon, Republic of Korea.

(Continued)

*Primary Examiner* — Joseph D Manoskey

(57) ABSTRACT

An electronic device including a memory storing an application program that provides a guide about a user action, collects information on a performance of the user action, or collects information on a user state. A processor connected to the memory is configured to execute the application program, to detect a cause by which the application program is stopped, and to automatically reexecute the application program or to provide a user interface for receiving a user input for the reexecution of the application program on the basis of at least a portion of the detected cause.

20 Claims, 9 Drawing Sheets

(51) Int. Cl.
*G06F 19/00* (2018.01)
*A61B 5/0205* (2006.01)
*A61B 5/0402* (2006.01)
*A61B 5/0476* (2006.01)
*A61B 5/0488* (2006.01)
*A61B 5/00* (2006.01)
*A63B 24/00* (2006.01)
*G16H 40/40* (2018.01)

(52) U.S. Cl.
CPC .......... *A61B 5/0476* (2013.01); *A61B 5/0488* (2013.01); *A61B 5/443* (2013.01); *A61B 5/4872* (2013.01); *A63B 24/0059* (2013.01); *A63B 24/0062* (2013.01); *A63B 24/0075* (2013.01); *G06F 11/1441* (2013.01); *G06F 19/3481* (2013.01); *G16H 40/40* (2018.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/62* (2013.01); *A63B 2220/74* (2013.01); *A63B 2225/50* (2013.01); *G06F 2201/805* (2013.01); *G06F 2201/85* (2013.01)

(58) Field of Classification Search
CPC ............. G06F 19/3412; G06F 19/3481; G06F 2201/805; G06F 2201/85; A61B 5/02055; A61B 5/0402; A61B 5/0476; A61B 5/0488; A61B 5/443; A61B 5/4872; A61B 24/0059; A61B 24/0062; A61B 24/0075; A63B 2220/12; A63B 2220/17; A63B 2220/20; A63B 2220/30; A63B 2220/40; A63B 2220/62; A63B 2220/74; A63B 2225/50
See application file for complete search history.

(56) References Cited

U.S. PATENT DOCUMENTS

| | | | |
|---|---|---|---|
| 2006/0271916 A1* | 11/2006 | Abe .................... | G06F 11/0715 717/128 |
| 2007/0162779 A1 | 7/2007 | Downer et al. | |
| 2010/0060586 A1 | 3/2010 | Pisula et al. | |
| 2012/0009906 A1 | 1/2012 | Patterson et al. | |
| 2012/0290109 A1 | 11/2012 | Engelberg et al. | |
| 2013/0102300 A1 | 4/2013 | Sigal et al. | |
| 2013/0305101 A1 | 11/2013 | Gupta et al. | |
| 2014/0031703 A1* | 1/2014 | Rayner .............. | A61B 5/02055 600/484 |
| 2014/0194150 A1 | 7/2014 | Wang et al. | |

OTHER PUBLICATIONS

European Patent Office, "European Search Report," Application No. 16176130.9, Oct. 20, 2016, 13 pages, publisher EPO, Munich, Germany, Place of search The Hague.

Thomas Homewood et al., "Skitracker: Measuring Skiing Performance using a Body Area Network," IT 13014, Examensarbete 45 hp, Feb. 28, 2013, 107 pages, publisher Uppsala Universitet, Uppsala, Sweden.

Sangwhan Cha et al., "Middleware Framework for Disconnection Tolerant Mobile Application Services," 8th Annual Communication Networks and Services Research Conference, 2010, pp. 334-340, publisher IEEE, Piscataway, New Jersey, USA.

E. Miluzzo; "Smartphone Sensing: A Thesis Submitted to the Faculty in partial fulfillment of the requirements for the degree of Doctor of Philosophy in Computer Science"; Dartmouth, College; Hanover, New Hampshire; Jun. 2011; 147 pages.

Foreign Communication from Related Counterpart Application; European Patent Application No. 16176130.9; Communication pursuant to Article 94(3) EPC dated Dec. 15, 2017; 6 pages.

* cited by examiner

OPERATING METHOD FOR APPLICATION PROGRAM AND ELECTRONIC DEVICE SUPPORTING THE SAME

CROSS-REFERENCE TO RELATED APPLICATION(S) AND CLAIM OF PRIORITY

The present application is related to and claims the benefit under 35 U.S.C. § 119(a) of a Korean patent application filed on Jun. 24, 2015 in the Korean Intellectual Property Office and assigned Serial number 10-2015-089769, the entire disclosure of which is hereby incorporated by reference.

TECHNICAL FIELD

The present disclosure relates to an operation of an application program run by an electronic device.

BACKGROUND

In recent years, as interest in health and wellness increases, interest in exercise as a way for maintaining health has also increased. With this trend toward a healthy lifestyle, an electronic device provides a workout function that helps a user to exercise more systematically and as planned. For instance, the electronic device may provide a workout function via a workout application that recommends appropriate physical activities or displays workout records to the user.

The above-described workout function of the electronic device is abnormally stopped depending on various circumstances causing the user to restart the workout function, which may be inconvenient. In addition, since it is difficult to check out the running state of the workout function during the exercise, the user may not notice, even though some workout records are missing, when the workout function is abnormally stopped during the exercise.

SUMMARY

To address the above-discussed deficiencies, it is a primary object to provide a method of operating an application program, which performs a specified operation depending on how the application program is stopped, to allow a user to more easily operate the application program, and an electronic device supporting the method.

In accordance with an aspect of the present disclosure, an electronic device includes a memory storing an application program that provides a guide about a user action and/or collects information on a user action performance and/or a user state and a processor connected to the memory. The memory stores instructions, and the instructions, when executed by the processor, causes the processor to execute the application program, to detect a cause by which the application program is stopped, and to automatically reexecute the application program or to provide a user interface for receiving a user input for the reexecution of the application program on the basis of at least a portion of the detected cause.

In accordance with an aspect of the present disclosure, a method of operating an application program includes determining stop of the application program while the application program is being executed, detecting a cause by which the application program is stopped, and processing to automatically reexecute the application program or to provide a user interface for receiving a user input for the reexecution of the application program on the basis of at least a portion of the detected cause.

According to various embodiments, specified operations may be executed in accordance with the stop state of the application program, and thus the operation of the application program may be easily supported.

Other aspects, advantages, and salient features of the disclosure will become apparent to those skilled in the art from the following detailed description, which, taken in conjunction with the annexed drawings, discloses various embodiments of the present disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

Throughout the drawings, it should be noted that like reference numbers are used to depict the same or similar elements, features, and structures.

DETAILED DESCRIPTION

Figure 1:
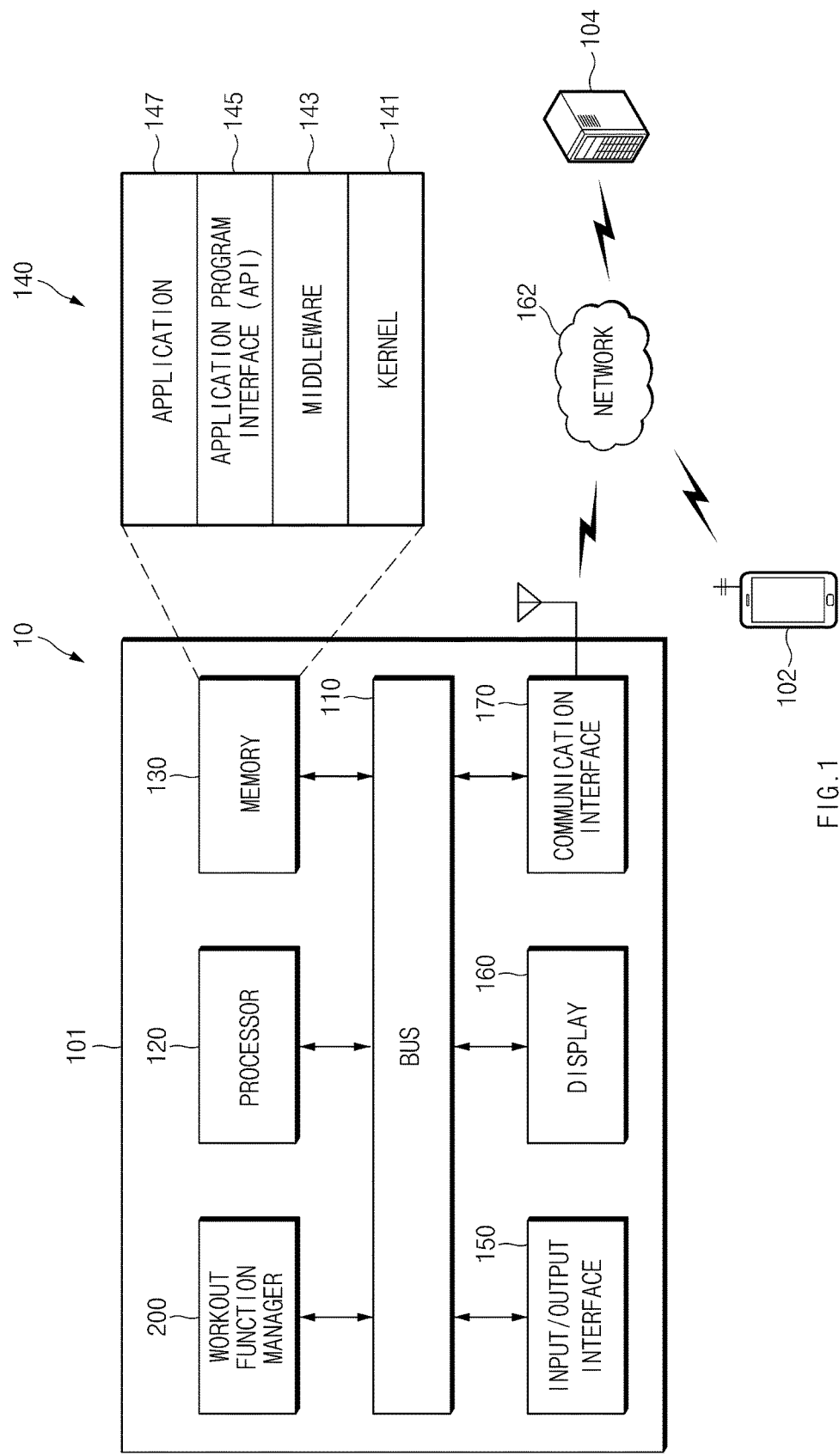
FIG. 1 illustrates an operational environment of an electronic device according to an embodiment of the present disclosure.

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

In the disclosure disclosed herein, the expressions "have", "may have", "include" and "comprise", or "may include" and "may comprise" used herein indicate existence of corresponding features (e.g., elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used herein may refer to various elements of various embodiments of the present disclosure, but do not limit the elements. For example, such terms do not limit the order and/or priority of the elements. Furthermore, such terms may be used to distinguish one element from another element. For example, "a first user device" and "a second user device" indicate different user devices. For example, without departing the scope of the present disclosure, a first element may be referred to as a second element, and similarly, a second element may be referred to as a first element.

It will be understood that when an element (e.g., a first element) is referred to as being "(operatively or communicatively) coupled with/to" or "connected to" another element (e.g., a second element), it can be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening element (e.g., a third element).

According to the situation, the expression "configured to" used herein may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to perform A, B, and C" may mean a dedicated processor (e.g., an embedded processor) for performing a corresponding operation or a generic-purpose processor (e.g., a central processing unit (CPU) or an application processor) which may perform corresponding operations by executing one or more software programs which are stored in a memory device.

Terms used in this specification are used to describe specified embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

Hereinafter, an electronic device will be described with reference to accompanying drawings according to various embodiments. In the disclosure disclosed herein, a term "user" used herein may refer to a person who uses an electronic device or may refer to a device (e.g., an artificial electronic device) that uses the electronic device.

FIG. 1 illustrates an operational environment of an electronic device according to an embodiment of the present disclosure.

Referring to FIG. 1, the electronic device operational environment 10 may include an electronic device 101, a network 162, a server 104, and an external electronic device 102.

The above-mentioned electronic device operational environment 10 may detect whether an abnormal stop of the electronic device 101 occurs based on a specified condition after the electronic device 101 executes an application program (e.g., at least one of a workout application program related to a workout function, a workout guide application program, a health-related application program, and a muscle making or building related application). In a case that the application program is abnormally stopped, the electronic device operational environment 10 may automatically rerun the application program and add a record to a stored activity record or stored activity information. Accordingly, the electronic device operational environment 10 may provide a function (e.g., a workout function) based on an appropriate application program without a separate operation of the user or in a state that the user does not recognize the abnormal stop of the application program.

According to various embodiments, the electronic device 101 may estimate an amount of missed activity caused by the stop of the application program corresponding to the abnormal stop of the electronic device 101. The electronic device 101 may add a record of the estimated amount of missed activity to the stored activity record such that a total amount of recorded activity is processed to become similar to a real activity amount. Therefore, the electronic device 101 may process a reward for achievement of the activity goal or a renewal of the record to be similar to those in a normal state of the activity amount.

The network 162 may support a wired communication channel or a wireless communication channel between the electronic device 101, the external electronic device 102, and the server 104. In addition, in a case where the external electronic device 102 includes a wireless communication interface, the network 162 may support the wireless communication channel for the external electronic device 102. The network 162 may include at least one device that supports a wireless communication function (e.g., various wireless communication manners of 2G, 3G, 4G, LTE, 5G, etc.), a wireless access communication function (e.g., a WIFI communication function), etc. The network 162 may also include a telecommunications network, i.e., at least one of a computer network (e.g., LAN or WAN) or a telephone network. In addition, the network 162 may include a short-range communication network. In this case, data may be transmitted and received between the electronic device 101 and the server 104, between the electronic device 101 and the external electronic device 102, or between the server 104 and the external electronic device 102 on the basis of a short-range communication channel.

The server 104 may be connected to the electronic device 101 through the network 162. The server 104 may form a wireless communication channel in response to a request from the electronic device 101. The server 104 may receive specific data from the electronic device 101. In addition, the server 104 may transmit specific data (e.g., a web page) to the electronic device 101.

The external electronic device 102 may include components same as or similar to those of the electronic device 101. According to an embodiment, the external electronic device 102 may form a sound or data communication channel with the electronic device 101.

The electronic device 101 may include a bus 110, a processor 120, a memory 130, an input/output (I/O) interface 150, a display 160, a communication interface 170, and a workout function manager 200. According to various embodiments, the electronic device 101 may further include a sensor module to collect sensor information in accordance with the execution of the application program. According to various embodiments, the electronic device 101 may receive sensor information from an external device (e.g., the external electronic device 102) in accordance with the execution of the application program without including a separate sensor module.

The bus 110 may interconnect the above-described components 110 to 180 and may be a circuit for conveying communications (e.g., a control message and/or data) among the above-described components. For instance, the bus 110 may connect the communication interface 170 and the workout function manager 200.

The processor 120 may include one or more of a central processing unit (CPU), an application processor (AP), or a communication processor (CP). The processor 120 may perform, for example, data processing or an operation associated with control and/or communication of at least one other component(s) of the electronic device 101. According to an embodiment, the processor 120 may install at least one application in response to a user input or specified schedule. The processor 120 may perform signal processing required to control and display a display state of at least one object displayed in the display 160 on the basis of a position at which an input event input through the display 160 supporting a touch function occurs. In this regard, the processor 120 may include at least a portion of the workout function manager 200 or at least one processor 120 may serve as at least a portion of the workout function manager 200.

The memory 130 may include a volatile and/or nonvolatile memory. The memory 130 may store instructions or data associated with at least one other component(s) of the electronic device 101. The instructions may be executed by at least one of the processor 120 or the workout function manager 200. The instructions may include instructions collecting a value of the position at which the input event occurs and instructions controlling at least one of the position and size of the objects displayed in the display 160 on the basis of the position at which the input event occurs. The instructions may include instructions outputting the object associated with the execution of the specified function to a predetermined position as viewed relative to the position at which the input event occurs. The instructions may include instructions processing a function corresponding to an event, which additionally occurs on a screen in which the display state of the object is controlled.

According to various embodiments, the memory 130 may be replaced with a storing device disposed outside the electronic device 101, such as a cloud server connected to the electronic device 101 through the communication interface 170. According to an embodiment, the memory 130 may exist inside/outside the electronic device as a storage space in which state information of the user using the electronic device is stored.

According to various embodiments, the memory 130 may store software and/or a program 140. The program 140 may include, for example, a kernel 141, a middleware 143, an application programming interface (API) 145, and/or an application program (or an application) 147. According to an embodiment, the program 140 may include a workout function application program.

At least a portion of the kernel 141, the middleware 143, or the API 145 may be called an "operating system (OS)". The kernel 141 may control or manage system resources (e.g., the bus 110, the processor 120, the workout function manager 200, the memory 130, and the like) that are used to execute operations or functions of other programs (e.g., the middleware 143, the API 145, and the application program 147). Furthermore, the kernel 141 may provide an interface that allows the middleware 143, the API 145, or the application program 147 to access discrete components of the electronic device 101 so as to control or manage system resources.

The middleware 143 may perform a mediation role such that the API 145 or the application program 147 communicates with the kernel 141 to exchange data. Furthermore, the middleware 143 may process task requests received from the application program 147 according to a priority. For example, the middleware 143 may assign the priority, which makes it possible to use a system resource (e.g., the bus 110, the processor 120, the workout function manager 200, the memory 130, or the like) of the electronic device 101, to at least one of the application program 147. For example, the middleware 143 may process the one or more task requests according to the priority assigned to the at least one application program, which makes it possible to perform scheduling or load balancing on the one or more task requests.

The API 145 may be an interface through which the application program 147 controls a function provided by the kernel 141 or the middleware 143 and may include, for example, at least one interface or function (e.g., an instruction) for a file control, a window control, an image processing, a character control, or the like.

The application 147 may include at least one application. For example, the application may include a music application, a workout (or health care) application, an alarm application, and the like. According to an embodiment, the application 147 may include a screen control application according to the touch input. The screen control application may be configured to include at least one program routine or instructions and may be included in other application(s) (e.g., a standby screen or home screen output application, a lock screen application, etc.).

The I/O interface 150 may perform an interface role to transmit an instruction or data, input from a user or another external device, to other component(s) of the electronic device 101. Furthermore, the I/O interface 150 may output an instruction or data, received from other component(s) of the electronic device 101, to a user or another external device. The I/O interface 150 may include, for example, at least one of a physical button, a touch button, a touch pad, or a touch screen. In addition, the I/O interface 150 may include an input unit, e.g., an electronic pen. Further, the I/O interface 150 may include an audio unit to process an audio signal. The audio unit may output audio data associated with the execution of the application. For example, the audio unit may output audio data corresponding to the occurrence of the touch event, sound effects corresponding to the display control on screen elements (e.g., objects). The output function of the audio data may be omitted by a program set or a user input.

According to various embodiments, the I/O interface 150 may include at least one of a keyboard, a camera, an external input device wired or wireless connected to the electronic device 100. According to various embodiments, the I/O interface 150 may include an input transmitted through communication(s) from a wearable device, a personal computer, a remote controller, or an electronic device of other users to control an operation of the electronic device of the user.

The display 160 may include, for example, a liquid crystal display (LCD), a light-emitting diode (LED) display, an organic LED (OLED) display, a microelectromechanical systems (MEMS) display, or an electronic paper display. The display 160 may display, for example, various contents (e.g., a text, an image, a video, an icon, a symbol, and the like) to a user. The display 160 may include a touch screen and may receive, for example, a touch, gesture, proximity, or hovering input using an electronic pen or a portion of a user's body.

The display 160 may output, for example, a lock screen including a lock pattern. In addition, the display 160 may output a standby screen or a home screen, which includes at least one icon. Further, the display 160 may output a web page screen. The display 160 may output a screen in which a display state of objects (e.g., lock pattern objects, icon objects, at least one object for the web page) included in the above-mentioned screens is controlled as viewed relative to a certain reference point associated with the input event. The display 160 may output a specified screen (e.g., an unlock screen, a function execution screen associated with a certain icon, or the like) in response to an additional input event.

The communication interface 170 may establish communication between the electronic device 101 and an external device (e.g., an external electronic device 102 or a server 104). For example, the communication interface 170 may be connected to the network 162 through wireless communication to communicate with the external device (e.g., the external electronic device 102 or the server 104). The communication interface 170 may receive a web page provided from the server 104. According to various embodiments, the communication interface 170 may receive data required to analyze a workout state of the user from the external device (e.g., the external electronic device 102) or may be connected to an external device for performing a guide to coaching a workout program.

The wireless communication may include at least one of, for example, long-term evolution (LTE), LTE Advance (LTE-A), code division multiple access (CDMA), wideband CDMA (WCDMA), universal mobile telecommunications system (UMTS), wireless broadband (WiBro), global system for mobile communications (GSM), or the like, as cellular communication protocol. Furthermore, the wireless communication may include, for example, a local area network. The local area network may include, for example, at least one of wireless fidelity (Wi-Fi), Bluetooth, near field communication (NFC), magnetic stripe transmission (MST), or global navigation satellite system (GNSS).

The GNSS may include, for example, at least one of global positioning system (GPS), Global Navigation Satellite System (GLONASS), BeiDou Navigation Satellite System (hereinafter, referred to as "BeiDou"), or Galileo, the European global satellite-based navigation system. Hereinafter, GPS and GNSS may be interchangeably used in the following descriptions. The wired communication may include at least one of, for example, a universal serial bus (USB), a high definition multimedia interface (HDMI), a recommended standard-232 (RS-232), or a plain old telephone service (POTS).

The sensor module may include, for example, at least one sensor to measure health state information associated with the user. A biometric information sensor used to measure the health state of the user may include a pedometer, a hemomanometer, a glucose meter, photoplethysmography (PPG), electrocardiogram (ECG), electromyography (EMG), electroencephalogram (EEG), an oxygen saturation measuring sensor, a skin moisture measuring sensor, an obesity meter, a body temperature sensor, and the like. As the biometric information sensor that recognizes individual biometric characteristics, a fingerprint sensor, an iris-recognition sensor, a face recognizer, a hand-shape recognizer, a hand-vein recognizer, a voice recognizer, and a handwritten signature recognizer may be used, and the biometric information sensor may include a camera, an IR camera, a touch sensor, a microphone, and the like. A health sensor may be a sensor that collects one or more biometric signals from the user. For example, the health sensor may collect raw data to measure at least one of a blood pressure, a blood flow, a heart rate (HRM, HRV), a body temperature, a breathing rate, an oxygen saturation, heart and lung sounds, a blood sugar, a waist size, a height, a weight, a body fat, a calorie consumption, a brainwave, a voice, a skin resistance, an electromyogram, an electrocardiogram, a gait, an ultrasonic image, a sleeping state, a facial expression, a pupil dilation, and an eye blink. The electronic device 101 may analyze the above-mentioned biometric signals, and thus the electronic device 101 may extract the biometric characteristic information. As an example, the biometric signals may include a pulse wave signal obtained through an HRV (Heart Rate Variability) sensor. The electronic device 101 may analyze the biometric signal to obtain primary biometric characteristic information, such as an average heart rate, a heart rate distribution, etc. In addition, the electronic device 101 may process the biometric characteristic information to obtain secondary biometric characteristic information, such as a stress state, a blood vessel aging degree, etc.

According to various embodiments, the health sensor may simply output the collected user biometric signals or may output the biometric characteristic information by analyzing the biometric signals through a processor built-in with the sensor. Accordingly, the biometric signals collected by the health sensor may be transmitted to a processor coupled to the sensor or a processor of a local device in which a sensor device is built and may be analyzed to generate the biometric characteristic information. For example, a mobile phone in which the ECG sensor is built may be used or a wrist watch in which the PPG sensor is built may be used. As another example, biometric signals collected by the HRV sensor built in an ear-clip may be transmitted to the wrist watch or a smart phone, and the device receiving the biometric signals may extract the biometric characteristic information. The extracted information may be transmitted to the device extracting the information or one or more other devices. If the biometric characteristic information are extracted by the smart phone, the wrist watch may output the biometric characteristic information provided from the smart phone to the display, and the ear-clip receiving the biometric characteristic information may output the biometric characteristic information through an audio processing module (e.g., speaker). According to various embodiments, the electronic device 101 may include a touch sensor, a key input sensor, an impact detecting sensor, a vibration detecting sensor, and the like and may sense connections with wired/wireless devices.

According to various embodiments, one sensor may sense two or more information. For example, an acceleration sensor may substantially simultaneously measure a motion and a step count of the user. As another example, the PPG sensor may be used as a sensor for biometric information, such as heart rate, stress, etc., or may be used as a proximity sensor based on a received light amount. As another example, the ECG sensor may recognize emotion, heart rate, and HRV (Heart Rate Variation) through an electrocardiogram analysis or may be used to certify the user.

According to various embodiments, at least one sensor included in the sensor module may be constantly driven when the electronic device is in a turn-on state. As another example, the sensor may be driven in accordance with a user input (e.g., a key input, a button input, a GUI input, a gesture recognition). As another example, when one sensor is driven, sensors associated with the driven sensor may be automatically driven. According to various embodiments, the sensor may be built in the electronic device, may be built in other external electronic devices, or may be installed at an external place (e.g., indoor, outdoor, building, base station, etc.).

The workout function manager 200 may control the display state of the screen objects according to the occurrence of the input event. For example, the workout function manager 200 may output the screen including at least one object to the display 160. When the input event is received, the workout function manager 200 may control the display state of the at least one object with respect to the position indicated by the input event. The workout function manager 200 may perform a specified function in response to an input event, which additionally occurs. According to various embodiments, when the additional input event satisfies a specified condition, the workout function manager 200 may perform the specified function, and when the additional input event does not satisfy the specified condition, the workout function manager 200 may control the screen to return to a state before the display state of the object is controlled. The workout function manager 200 may be provided as at least one processor or as a part of the processor. In addition, at least a portion of the workout function manager 200 may be provided as a program routine in the form of software, and thus the workout function manager 200 may be loaded on a certain processor or implemented by the certain processor. At least a portion of the workout function manager 200 may be provided in the form of software. In this case, at least the portion of the workout function manager 200 may be operated by the processor 120. As another way, at least the portion of the workout function manager 200 may be provided in the form of hardware. In this case, at least the portion of the workout function manager 200 may be realized by the processor 120.

Figure 2:
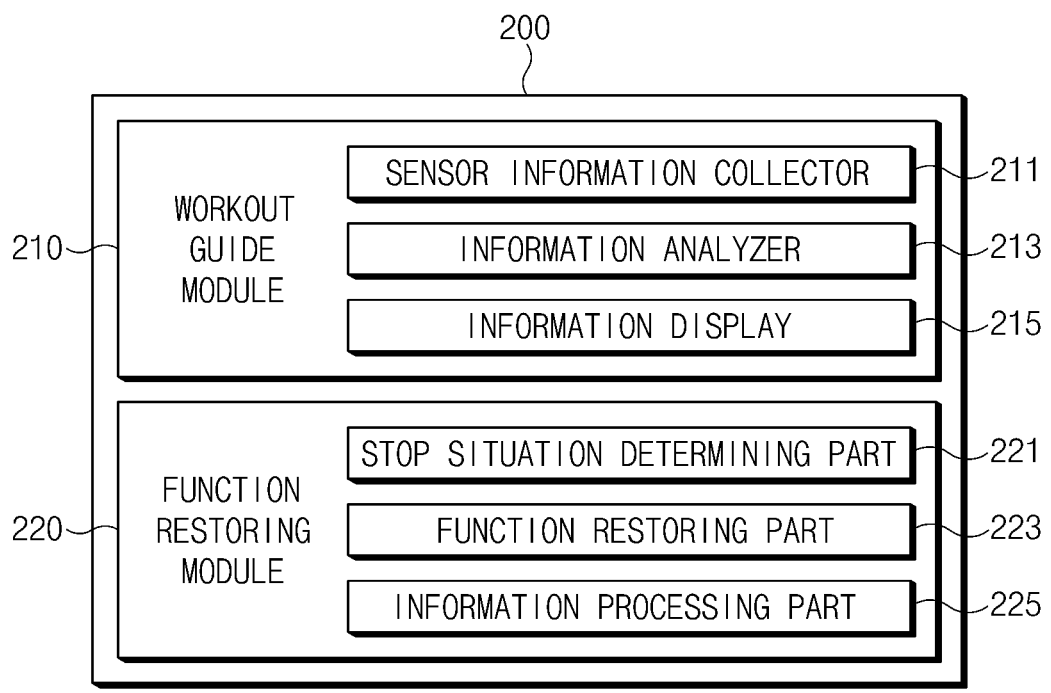
FIG. 2 illustrates an example of a workout function manager according to an embodiment.

FIG. 2 illustrates an example of a workout function manager according to an embodiment.

Referring to FIG. 2, the workout function manager 200 may include a workout guide module 210 and a function restoring module 220.

The workout guide module 210 may support an application program of the electronic device 101, e.g., an operation of a workout function application program. For example, the workout guide module 210 may execute the application program in response to the user input or predetermined scheduling information. In this operation, the workout guide module 210 may utilize a workout service module (e.g., a software or hardware module that is designed to activate at least one sensor and collect the activated sensor information) associated with the execution of the application program. To achieve set of workout targets, the workout guide module 210 may verify the user's compliance with the workout program by using the user's activity measured by a sensor part or the amount of the activity, and thus the workout guide module 210 may provide a workout program suitable for user's situation changes.

The workout service module may be activated while the electronic device 101 is booted, and then the workout service module may basically support the sensor operation and collect the sensor information. When the application program is executed, the workout service module may provide the collected sensor information to the workout guide module 210. The workout service module may be operated to collect and store the sensor information while the application program is stopped or after the stop of the application program. The abnormal stop of the application program or the abnormal stop of the electronic device 101 may include, for example, a case that the application program is crashed by an error in the application or system and a case that the system stops the application in response to the reexecution of the application in accordance with the change of attributes of the system. In addition, according to various embodiments, the abnormal stop of the application program may include a case that the application is forcibly stopped by a user input, a case that the electronic device 101 is turned off corresponding to out of battery, a case that the electronic device 101 is abnormally powered off by a detachment of battery or an error in hardware (HW) or operating system (OS), a case that the electronic device 101 is shut down by a user's mistake, and the like. The non-activated workout service module may be automatically activated again by a booting schedule when the electronic device 101 is rebooted. In addition, the non-activated workout service module may be automatically reactivated by a process of a system (e.g., an operating system). In this regard, the workout guide module 210 may include a sensor information collector 211, an information analyzer 213, and an information display 215.

The sensor information collector 211 may collect specified sensor information in accordance with the execution of the application program. For example, the sensor information collector 211 may request certain sensor information (e.g., acceleration sensor information, pedometer operation information, barometer operation information, speed sensing information, direction sensing information, distance sensing information, etc.) to the workout service module. The workout service module may collect associated sensor information in response to the request from the sensor information collector 211 and provide the collected sensor information to the sensor information collector 211. Here, the workout service module may activate a certain sensor in accordance with the request from the sensor information collector 211 to provide the sensor information according to the operation of the activated sensor to the sensor information collector 211. The sensor information collector 211 may provide the information analyzer 213 with the collected sensor information.

The information analyzer 213 may analyze the sensor information provided thereto to analyze the amount of activity. For example, the information analyzer 213 may analyze at least one of a moving distance, a moving direction, and a moving speed on the basis of position information (or GPS information). In addition, the information analyzer 213 may analyze an altitude variation during workout based on altitude information (or barometer information). In addition, the information analyzer 213 may correct the moving distance, direction, and speed calculated based on the GPS information with the speed sensing information or the pedometer operation information. According to various embodiments, the information analyzer 213 may provide information representing whether the workout targets are achieved, information representing remaining amount of activity to achieve the workout targets, information representing the reward for the achievement of the workout targets to the information display 215 by comparing the analyzed information with the set of workout targets.

The information display 215 may output the information provided from the information analyzer 213 to the display 160 or may convert the information into specified audio data to output the converted audio data through an audio device. For example, the information display 215 may output current activity amount information (e.g., a moving distance, a moving route, a moving speed, etc.). In addition, the information display 215 may output information on the target amount of workout, information on current amount of workout, information on the remaining amount of workout, and the like.

The function restoring module 220 may restore (e.g., reexecution) the application program that is abnormally stopped. The function restoring module 220 may be included in the application program. As another example, the function restoring module 220 may be included in the workout service module. In addition, the function restoring module 220 may be provided as a separate software module or hardware module and included in the booting schedule, and thus the function restoring module 220 may be operated during the booting process.

According to various embodiments, the function restoring module 220 may register a function restoring request on the OS in response to the execution of the application program. According to an embodiment, in a case that the electronic device is operated in a specific operating system (e.g., android operating system), the function restoring module 220 (or the workout guide module 210) may be executed at a background in the form of android service and may register a flag on an android framework to allow the function restoring module 220 to be executed again while being abnormally stopped. The android framework may restart the registered service in the case that the service is abnormally stopped while monitoring various services, and in this case, the function storing module 220 (or the workout guide module 210) may recognize that the function storing module 220 is restarted after being abnormally stopped. In the case where the workout guide module 210 performs a request of the automatic restart corresponding to the abnormal stop, the workout guide module 210 may request the system to call the function restoring module 220 when the automatic restart is performed in accordance with the abnormal stop. Accordingly, the function restoring module 220 may stand by while the application program is normally executed and may be executed by the call from the system in the case that the application program is abnormally stopped.

According to various embodiments, the specific operating system may forcibly stop all of the processes generated by a specific application in response to the user input. In this case, since the application is stopped by the user input, a framework (e.g., android framework) of the specific operating system may process a corresponding application such that the corresponding application is not automatically operated even though the service registers the flag for its restart. The operating system may notify the fact that the electronic device 101 is booted to an application that requires the fact and may support operations required for the booting stage.

In association with the above-mentioned function support, the function restoring module 220 may include a stop situation determining part 221, a function restoring part 223, and an information processing part 225.

The stop situation determining part 221 may determine the stop situation when the application program is stopped. For example, in the case that the application program is stopped, the stop situation determining part 221 may analyze an event occurring before the stop of the application program to determine whether the application program is abnormally stopped or normally stopped. According to an embodiment, the stop situation determining part 221 may verify whether a user input event (e.g., a virtual button selection input signal provided to request the stop of the workout function application program) associated with the normal stop occurs before the stop of the application program. As another way, the stop situation determining part 221 may determine the stop of the application program as the abnormal stop when the application program is stopped in accordance with specified conditions. For example, the stop situation determining part 221 may determine that the stop of the application program corresponding to the occurrence of events associated with system changes, such as a change in background screen, a change in user information, etc., is the abnormal stop to automatically restart the application program. In addition, when the application program is stopped in accordance with the execution of the application program and other certain application program, the stop situation determining part 221 may determine that the stop of the application program is the abnormal stop to automatically restart the application program.

According to various embodiments, when the application program is stopped due to the out of battery, the detachment of battery, the forcible stop of the application by the user, or the reception of the user input signal, the stop situation determining part 221 may determine that the stop of the application program is to manually execute the application program. When the application program is stopped, the stop situation determining part 221 may transmit stop situation information to the function restoring part 223.

The function restoring part 223 may differently process a function restoring operation in accordance with the information provided from the stop situation determining part 221. For example, in the case that the application program is abnormally stopped by the specified condition, the function restoring part 223 may automatically reexecute the application program. According to an embodiment, the function restoring part 223 may request a registration, which requests the restoration of the application program, to the system. When the application program is abnormally stopped by the specified condition, the system may automatically reexecute the application program in response to the request from the function restoring part 223. The function restoring part 223 may request a workout record recorded by the automatically-reexecuted application program to the workout guide module 210. In this case, the function restoring part 223 may request the information processing part 225 to estimate the amount of workout.

The information processing part 225 may collect first workout record information obtained right before the application program is abnormally stopped and second workout record information obtained right after the application program is reexecuted. The information processing part 225 may estimate the workout amount based on the obtained first workout record information and the obtained second workout record information. For example, the information processing part 225 may calculate an estimated moving distance by comparing first position information included in the first workout record information with second position information included in the second workout record information. The information processing part 225 may calculate a time duration by comparing first time information included in the first workout record information with second time information included in the second workout record information. The information processing part 225 may calculate an estimated moving speed based on the time duration and the estimated moving distance. In addition, the information processing part 225 may calculate an altitude variation in the estimated moving distance by comparing first altitude information included in the first workout record information with second altitude information included in the second workout record information.

The information processing part 225 may calculate the workout amount based on the estimated moving distance, the estimated moving speed, and the altitude variation of the estimated moving distance. According to an embodiment, the information processing part 225 may calculate a relatively large estimated amount of workout in the case that the altitude variation of the estimated moving distance is relatively large even though the estimated moving distance is constant. In addition, the information processing part 225 may calculate a relatively large estimated amount of workout in the case that the estimated moving speed is relatively large even though the estimated moving distance is constant. The information processing part 225 may transmit the estimated moving distance, the estimated moving speed, the altitude variation of the estimated moving distance, and the estimated workout amount to the workout guide module 210.

According to various embodiments, the workout guide module 210 (e.g., the information analyzer 213) may apply the estimated workout amount to a section in which no workout record exists due to the abnormal stop on the basis of the information provided from the information processing part 225. In addition, the workout guide module 210 may aggregate a previous work amount, the estimated workout amount, and the workout amount after the reexecution to provide workout guide information (e.g., achievement of workout targets, remaining amount of activity to achieve the workout targets, etc.).

According to various embodiments, an electronic device according to an embodiment may include a memory into which the application program is stored and a processor connected to the memory, the processor may automatically reexecute the application program in a case that the application program is stopped in accordance with a specified first condition, and the processor may output information to verify whether the application program is reexecuted in a case that the application program is stopped in accordance with a specified second condition.

According to various embodiments, the processor may automatically reexecute the application program in a case that the application program is stopped corresponding to a system information generation while the application program (e.g., a workout function application program) is executed.

According to various embodiments, the processor may automatically reexecute the application program when the application program is stopped during the generation of at least one of reception of call connection request information from an external electronic device, reception of message information, reception of application execution request information, which is different from the application program, change in background screen, change in theme, and arrival of specified schedule.

According to various embodiments, the processor may output the information to verify whether the application program is reexecuted when the application program is stopped by receiving user input information associated with the operation of the application program or by state change occurrence associated with a battery of the electronic device.

According to various embodiments, the processor may output information to verify whether the application program is reexecuted in accordance with at least one of reception of input information corresponding to a stop button selection in an execution screen of the application program, reception of input information required to remove the application program in a screen where an application program list is displayed, a battery discharge, a change of a voltage level of the battery to be lower than a predetermined voltage level, and a disconnection of the battery.

According to various embodiments, the processor may calculate the estimated workout amount based on first workout information when the application program is stopped and second workout information when the application program is automatically reexecuted or reexecuted in accordance with the input, and the processor may set the estimated workout amount to a workout amount between the time point at which the application program is stopped and the time point at which the application program is reexecuted.

According to various embodiments, the processor may calculate the estimated moving distance based on the position information of the first workout information and the position information of the second workout information.

According to various embodiments, the processor may calculate the altitude variation of the estimated moving distance based on the altitude information of the first workout information and the altitude information of the second workout information.

According to various embodiments, the processor may output guide information with respect to the automatic reexecution of the application program when the application program is reexecuted.

According to various embodiments, when the application program is reexecuted in accordance with the user input, the processor may add the workout record obtained by the reexecution of the application program to the workout information recorded until the application program is stopped.

Figure 3:
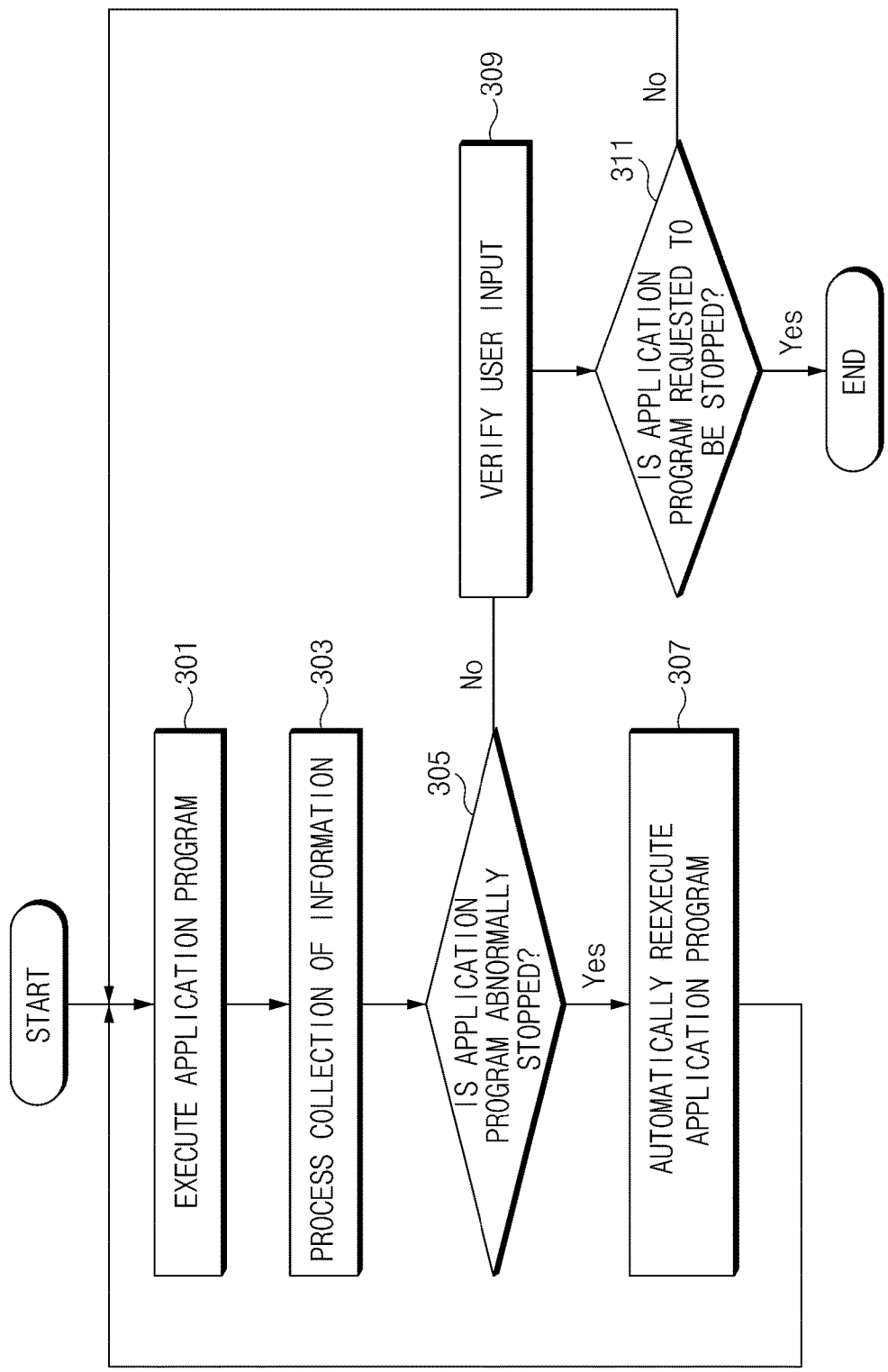
FIG. 3 illustrates a flowchart of a method of operating an application program according to an embodiment.

FIG. 3 illustrates a flowchart of a method of operating an application program according to an embodiment.

Referring to FIG. 3, in operation 301 of the operating method of the application program, the electronic device 101 may execute the application program (e.g., the workout function application program). In this regard, the electronic device 101 may output an icon or menu associated with the execution of the application program through the display 160. The electronic device 101 may execute the application program when the icon or the menu is selected. As another way, the electronic device 101 may execute the application program in accordance with the specified scheduling event.

In operation 303, the electronic device 101 may perform the operation of collecting the workout information. The electronic device 101 may record the workout amount based on the sensor information in accordance with the execution of the application program. The electronic device 101 may provide the workout guide information depending on the settings. The workout guide information may include, for example, information on set of target workout amount, information required for the user to achieve the target workout amount, information on remaining workout amount for the achievement of the target workout amount on the basis of the workout performance, success or failure in achievement of the workout target, reward determined based on the workout record when achieving the workout target, and the like.

In operation 305, the electronic device 101 may verify whether the abnormal stop of the application program occurs. The abnormal stop of the application program may include, for example, the stop according to the specified condition. According to an embodiment, the abnormal stop of the application program may include a case that the application program is stopped when other applications are executed during the execution of the application program. In addition, the abnormal stop of the application program may include a case that the application program is stopped by the execution of the system change (e.g., a default setting or a user setting of the operating system or the electronic device 101) in accordance with the user operation on the electronic device 101.

When the abnormal stop of the application program occurs, the electronic device 101 may perform the automatic reexecution of the application program in operation 307. In this regard, the system of the electronic device 101 may perform the registration of the system (e.g., operating system) to allow the application program to be automatically reexecuted when the application program is abnormally stopped in accordance with abnormal stop conditions of the application program during the execution of the application program. After the automatic reexecution of the application program, the electronic device 101 may automatically add the workout record In this regard, the electronic device 101 may add a workout record input after the reexecution of the application program to the workout record obtained right before the abnormal stop of the application program.

According to various embodiments, the electronic device 101 may output the guide information about the automatic reexecution of the application program. For example, the electronic device 101 may output the guide information (e.g., information on a reason why the application program is abnormally stopped during the execution of the application program) to the display 160 after the application program is automatically reexecuted. The guide information may be removed after temporarily being displayed in the display 160.

In the case that the application program is normally stopped, the electronic device 101 may perform a process to verify the user input in operation 309. In this regard, for example, the electronic device 101 may display a user interface or a graphic user interface (GUI), e.g., a popup window, to select the reexecution or stop of the application program. According to an embodiment, the electronic device 101 may display a popup window related to the reexecution of the application program right after the stop of the application program. According to various embodiments, in the case that the electronic device 101 is rebooted after the electronic device 101 is turned off due to the battery discharge or the battery detachment, the electronic device 101 may display a popup window asking whether the application program is reexecuted. According to various embodiments, when the application program is stopped by the forcible stop of the application program by the user, the electronic device 101 may display a popup window asking whether the application program is reexecuted.

According to various embodiments, the forcible stop of the application program may include a stop caused by a user control in addition to the stop caused by selecting the virtual button assigned to stop the application program. For example, the forcible stop of the application program may occur by reception of an input signal to stop the application program in a search screen of all of executed applications. As another way, the forcible stop of the application program may occur due to removal of memory allocation for a presently executed application or reception of an input signal requesting to stop the execution of the application in a set screen of the application. According to an embodiment, the forcible stop of the application program may occur by an input signal (e.g., a swipe event) that stops the execution of the application program in the application search screen displayed by selecting the home key.

In operation 309, when the user input is generated to request the reexecution of the application program, the electronic device 101 may reexecute the application program. When the input signal is received to verify the stop of the application program, the electronic device 101 may stop the application program and perform the specified function.

In operation 311, the electronic device 101 may verify whether the stop of the application program is requested after the application program is reexecuted. In the case that the stop request for the application program is not generated, the electronic device 101 may proceed to the execution of the application program in operation 301 and may reexecute the operations following the execution of the application program. In the case that the stop request for the application program is generated, the electronic device 101 may stop the application program and execute the specified function. For example, the electronic device 101 may output the workout record recorded during the execution of the application program and the workout analysis information analyzed during the execution of the application program.

Figure 4:
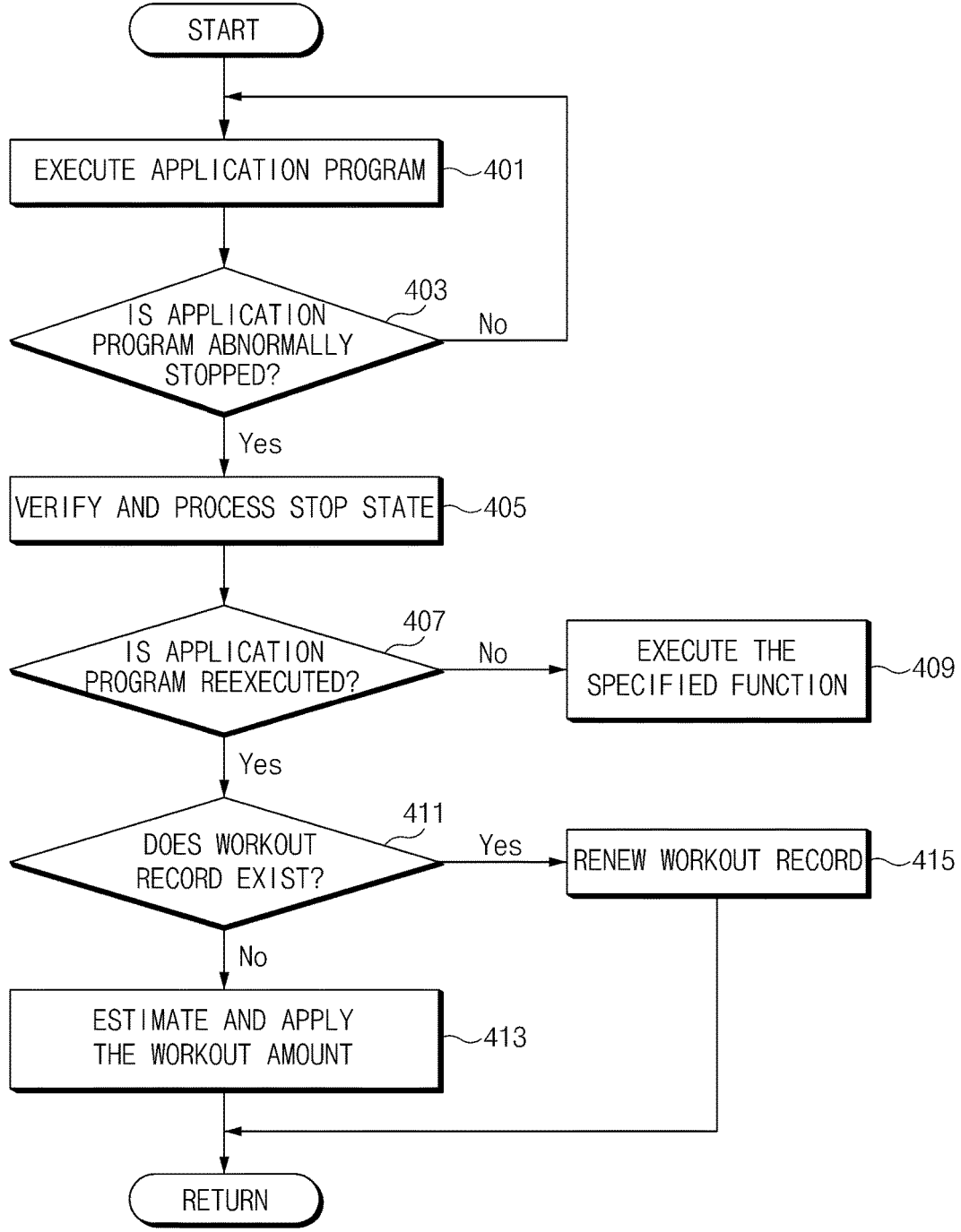
FIG. 4 illustrates a flowchart of another method of operating an application program according to an embodiment.

FIG. 4 illustrates a flowchart of another method of operating an application program according to an embodiment.

Referring to FIG. 4, in operation 401 of the operating method of the application program, the electronic device 101 may execute the application program (workout function application program). For example, the electronic device 101 may execute the application program in accordance with the user input requesting the execution of the application program or arrival of specified schedule. The electronic device 101 may record the workout based on the sensor information or may output the workout guide information in accordance with the execution of the application program.

In operation 403, whether the application program is stopped may be verified. When the application program is not stopped, the electronic device 101 may proceed to operation 401 to maintain the execution of the application program. When the application program is stopped, the electronic device 101 may verify the stop state and perform an operation based on the verified result in operation 405. For example, the electronic device 101 may verify in what situation the application program is stopped. In this operation, when the application program is stopped in accordance with a specified first condition, the electronic device 101 may automatically reexecute the application program. When the application program is stopped in accordance with a specified second condition, the electronic device 101 may display the popup window asking whether the application program is reexecuted. When the input signal requesting the reexecution of the application program is received through the popup window, the application program may be reexecuted. When the input signal related to the verification of the stop of the application program is received, the electronic device 101 may process specified functions (e.g., output of a guide on the stop of the workout function application program, output of workout record information recorded during the execution of the workout function application program, guide on the workout guide stop, etc.).

The first condition may include, for example, a case that the application program is stopped due to the system information generation while the workout is continuously executed. The system information may include, for example, call connection request information from an external electronic device, message reception information, application execution request information different from the application program, change in background screen, change in theme, arrival of specified schedule, and the like. The second condition may include, for example, the reception of user input information associated with operation of the application program or the state change associated with the battery of the electronic device 101. The user input information associated with the operation of the application program may include the input information corresponding to the stop button selection in the execution screen of the application program, the input information required to remove the application program in the screen where the application program list is displayed. The state change associated with the battery may include, for example, the battery discharge, the change of the voltage level of the battery to be lower than the predetermined voltage level, the disconnection of the battery, etc.

In operation 407, the electronic device 101 may verify whether the application program is reexecuted. As described above, the electronic device 101 may automatically reexecute the application program or may reexecute the application program in response to the user input within a specified time. When the application program is not reexecuted, the electronic device 101 may execute the specified function in operation 409. According to various embodiments, when the application program is reexecuted after the specified time lapses, the electronic device 101 may determine that the reexecution of the application program is a request for executing a new application program, and thus the electronic device 101 may output a new workout record and a new workout guide.

When the application program is reexecuted, the electronic device 101 may verify whether the workout record information exist between the stop of the workout and the reexecution of the application program in operation 411. When the workout record information does not exist, the electronic device 101 may estimate and apply the workout amount in operation 413. For example, the electronic device 101 may estimate the workout amount based on the information obtained right before the stop of the application program and the information obtained right after the reexecution of the application program. According to an embodiment, the electronic device 101 may calculate workout estimation information including at least one of the estimated moving distance, the estimated moving speed, the estimated moving direction, and the altitude variation of the estimated moving distance on the basis of the information obtained right before the stop of the application program and the information obtained right after the reexecution of the application program. The electronic device 101 may apply the estimated workout amount as a workout amount performed between the stop of the application program and the reexecution of the application program.

When the workout record information exist, the electronic device 101 may perform a renewal of the workout record in operation 415. For example, in the case that the workout service module is operated even though the application program is stopped in accordance with the forcible stop or the normal stop of the application program, the electronic device 101 may continuously record the workout record information in accordance with the reexecution of the application program.

Figure 5:
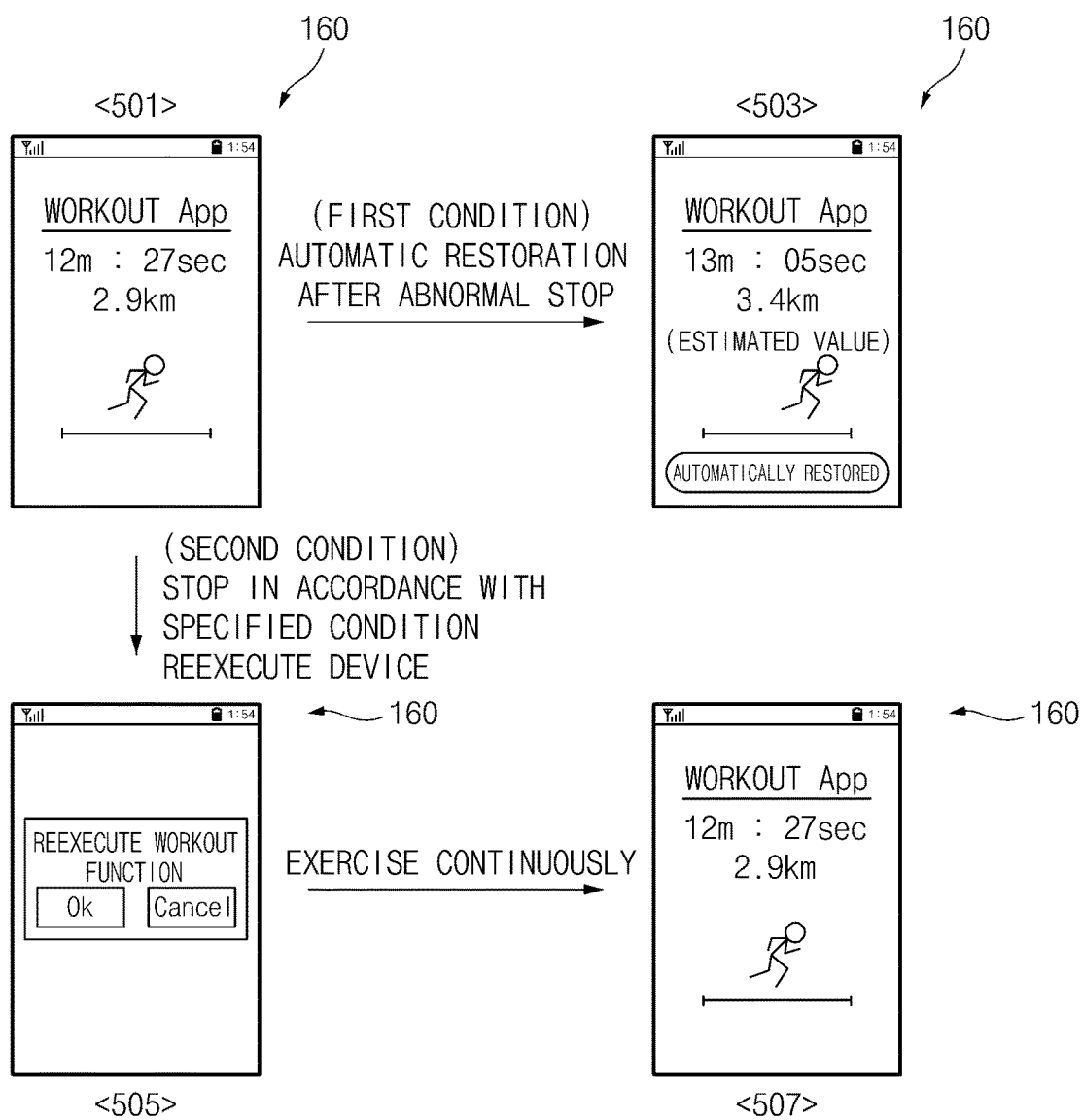
FIG. 5 illustrates an example of a screen interface of an electronic device according to an embodiment.

FIG. 5 illustrates an example of a screen interface of an electronic device according to an embodiment.

Referring to FIG. 5, the electronic device 101 may collect the sensor information in response to the execution request for the application program. The electronic device 101 may analyze the collected sensor information to record the workout amount. Accordingly, the electronic device 101 may display the workout amount of the current time through the display as shown in a state 501. Additionally, the electronic device 101 may display information, e.g., the target workout amount, the remaining workout amount to the target, etc.

According to an embodiment, when an automatic restoring function is executed after the abnormal stop (e.g., the stop according to the first condition), the electronic device 101 may display the application program screen through the display 160 in accordance with the automatic restoring of the application program as shown in a state 503. In addition, the electronic device 101 may output guide information to guide the automatic restoring of the application program. A function of outputting the guide information may be omitted depending on a variation in design or in user set. Further, the electronic device 101 may calculate the estimated workout amount for a time between the stop of the application program and the reexecution of the application program. The electronic device 101 may output the information on the estimated workout amount to the display 160. According to various embodiments, the electronic device 101 may notify that an estimated value is included in the workout amount information when the electronic device 101 outputs the workout amount information obtained by adding the estimated workout amount and a previous workout amount. According to various embodiments, the electronic device 101 may separately output the workout amount before the stop of the application program and the estimated workout amount. In addition, the electronic device 101 may separately output the current workout amount, the workout amount before the stop, and the estimated workout amount, or the electronic device 101 may aggregate the total amount of workout to output the total amount of workout.

According to various embodiments, when the device is reexecuted after being stopped in accordance with the specified condition (e.g., the second condition different from the first condition), the electronic device 101 may output the popup window for the reexecution of the application program to the display as shown in a state 505. When the input signal requesting the reexecution of the application program (or an input signal requesting to continue the workout) is received, the electronic device 101 may reexecute the application program and continuously record the workout record as shown in a state 507. In this operation, the electronic device 101 may ignore an interval between the stop of the application program and the reexecution of the application program and start recording the current workout amount in addition to the previous workout amount obtained before the stop of the application program.

Figure 6:
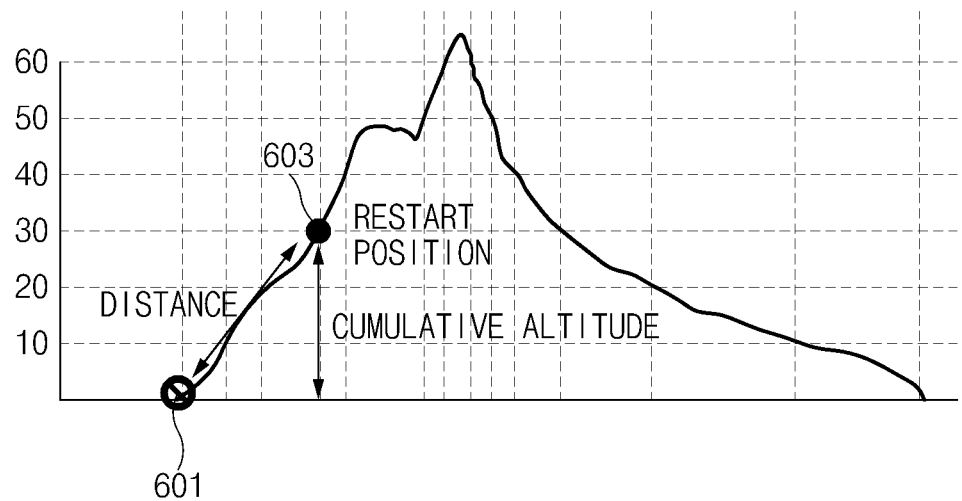
FIG. 6 illustrates a method of calculating an estimated workout according to an embodiment.

FIG. 6 illustrates a method of calculating the estimated workout amount according to an embodiment.

Referring to FIG. 6, according to various embodiments, a time point at which the workout is resumed after the stop of the workout may not be the time point at which the abnormal stop occurs. In case of a workout that moves rapidly, such as cycling, jogging, etc., a position of the time point at which the workout is resumed may be different from a position of the time point at which the abnormal stop occurs. In this case, the time point of the workout resume may be changed by estimating the workout amount before the workout is resumed. According to various embodiments, as a factor to be considered to resume the workout, at least one of position, distance, speed, user's profile (height, weight, etc.,), altitude, recovery delay time, and the like may be included.

For example, after the application program is executed, the abnormal stop of the application program may occur at a point 601. The electronic device 101 may collect and record the workout amount according to the execution of the application program and store only the record of the workout amount before the point 601.

Then, the application program may be automatically reexecuted or may be reexecuted in response to the user input at a point 603 after a predetermined time lapses. In this case, the electronic device 101 may calculate the estimated workout amount on the basis of information on the point 601 and information on the point 603. According to an embodiment, the electronic device 101 may determine a straight distance between the point 601 and the point 603 as the moving distance and process the lapse of time as the workout time. In addition, the electronic device 101 may estimate the workout amount depending on the variation in altitude on the basis of a value of straight line connecting the altitude information on the point 601 and the altitude information on the point 603.

According to various embodiments, the electronic device 101 may determine the distance connecting the point 601 and the point 603 on the basis of map information. For example, the electronic device 101 may calculate the estimated moving distance using a shortest distance (including a detour distance in a case that buildings exist) between the point 601 and the point 603 except for a section in which buildings exist or a distance to which a specified compensation rate is applied (e.g., a distance extracted longer than a straight line by applying the specified compensation rate to the straight line). The electronic device 101 may calculate a calorie consumption as a function of the distance by applying a moving distance during the stop period, the weight of the user (collected by the user input), and altitude variation value. The electronic device 101 may calculate an average speed by dividing the moving distance during the stop period (e.g., a period between the stop of the application program and the reexecution of the application program) by the time duration.

According to various embodiments, when the application program is stopped by the first condition or the second condition described with reference to FIGS. 4 and 5, the electronic device 101 may communicate with an external device (e.g., a companion device, an electronic watch, etc.) and request to measure the workout amount. The electronic device 101 may request the measured workout amount to the external device when the application program is reexecuted. The electronic device 101 may replace the above-mentioned estimated workout amount with the workout amount provided from the external device. According to various embodiments, the electronic device 101 may not request the measurement of the workout amount to the external device in the case that the application program is automatically reexecuted in accordance with the stop of the application program corresponding to the first condition and may request the measurement of the workout amount to the external device in the case that the application program is stopped in accordance with the second condition.

According to various embodiments, to determine the resume timing of the workout after the stop of the workout, the electronic device 101 may utilize information obtained from peripheral devices that may communicate with the electronic device 101. For example, the electronic device 101 may receive information on the user's activity measured by a wearable device to estimate a variation amount in workout of the user during the recovery time, and the estimated variation amount in workout may be utilized to determine the resume timing of the workout. According to an embodiment, the electronic device 101 may collect information on the workout amount of the user during the recovery time by utilizing information collected through peripheral devices, such as treadmill, camera, thermometer, odometer, etc., which monitor the workout state of the user, and thus the collected information on the workout amount may be utilized to determine the resume timing of the workout.

As described above, various embodiments may determine whether the application program is automatically resumed or manually resumed in consideration of conditions of the electronic device and the user when the application program is abnormally stopped during the workout and may provide the resuming method of the application program, and as a result, the workout resume function may be efficiently improved, and a loss of the workout record, which is caused by the abnormal stop of the application program, may be compensated.

According to the above-mentioned various embodiments, the operating method of the application program may include the operation of recording the workout amount in accordance with the execution of the application program of the electronic device, the operation of automatically reexecuting the application program in the case that the application program is stopped in accordance with the specified first condition, and the operation of outputting the information to confirm whether the application program is reexecuted in the case that the application program is stopped in accordance with the specified second condition.

According to various embodiments, the processing operation may include the operation of automatically reexecuting the application program in the case that the application program is stopped by the occurrence of the system information during the execution of the application program.

According to various embodiments, the processing operation may include the operation of automatically reexecuting the application program when the application program is stopped during the generation of at least one of reception of call connection request information from the external electronic device, reception of message information, reception of application execution request information, which is different from the application program, change in background screen, change in theme, and arrival of specified schedule.

According to various embodiments, the processing operation may include the operation of outputting information for verifying whether the application program is reexecuted when the application program is stopped by receiving the user input information associated with the operation of the application program or by the state change occurrence associated with a battery of the electronic device.

According to various embodiments, the processing operation may include the operation of outputting information for verifying whether the application program is reexecuted in accordance with at least one of reception of the input information corresponding to the stop button selection in the execution screen of the application program, reception of the input information required to remove the application program in the screen where an application program list is displayed, the battery discharge, the change of the voltage level of the battery to be lower than the predetermined voltage level, and the disconnection of the battery.

According to various embodiments, the method may further include the operation of calculating the estimated workout amount based on the first workout information obtained when the application program is stopped and the second workout information obtained when the application program is automatically reexecuted and the operation of processing the estimated workout amount to the workout amount between the time point at which the application program is stopped and the time point at which the application program is reexecuted.

According to various embodiments, the operation of calculating the workout amount may include the operation of calculating the estimated moving distance based on the position information of the first workout information and the position information of the second workout information.

According to various embodiments, the operation of calculating the workout amount may include the operation of calculating the altitude variation of the estimated moving distance based on the altitude information of the first workout information and the altitude information of the second workout information.

According to various embodiments, the method may further include the operation of outputting the guide information on the automatic execution of the application program.

According to various embodiments, the method may further include the operation of adding the workout record obtained by reexecuting the application program when the application program is reexecuted by the user input to the workout information recorded until the application program is stopped.

Figure 7:
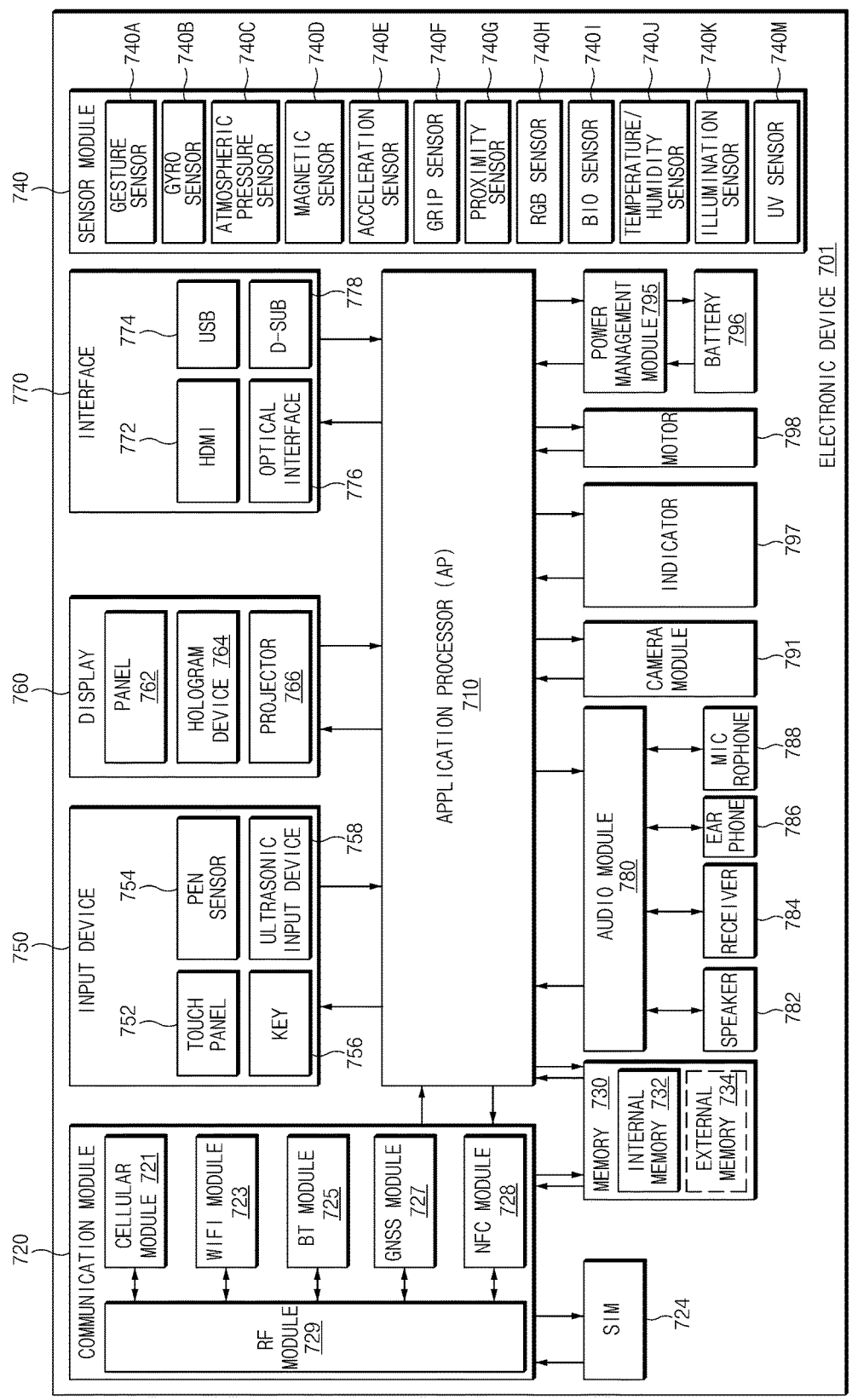
FIG. 7 illustrates a block diagram of an electronic device according to an embodiment.

FIG. 7 illustrates a block diagram of an electronic device according to an embodiment.

Referring to FIG. 7, an electronic device 701 may include, for example, all or a part of an electronic device 101 illustrated in the above-mentioned various embodiments. The electronic device 701 may include one processor (e.g., an application processor (AP)) 710, a communication module 720, a subscriber identification module 724, a memory 730, a sensor module 740, an input device 750, a display 760, an interface 770, an audio module 780, a camera module 791, a power management module 795, a battery 796, an indicator 797, and a motor 798.

The processor 710 may drive an operating system (OS) or an application program to control a plurality of hardware or software components connected to the processor 710 and may process and compute a variety of data. The processor 710 may be implemented with a system on chip (SoC), for example. According to an embodiment of the present disclosure, the processor 710 may further include a graphic processing unit (GPU) and/or an image signal processor. The processor 710 may include at least a part (e.g., a cellular module 721) of components illustrated in FIG. 7. The processor 710 may load and process an instruction or data, which is received from at least one of other components (e.g., a nonvolatile memory), and may store a variety of data at a nonvolatile memory.

The communication module 720 may be configured the same as or similar to a communication interface 170 of FIG. 1. The communication module 720 may include a cellular module 721, a Wi-Fi® module 723, a Bluetooth® (BT) module 725, a GNSS module 727 (e.g., a GPS module, a GLONASS module, a BeiDou module, or a Galileo module), a near field communication (NFC) module 728, and a radio frequency (RF) module 729.

The cellular module 721 may provide voice communication, video communication, a text service, an Internet service or the like through a communication network. According to an embodiment, the cellular module 721 may perform discrimination and authentication of the electronic device 701 within a communication network using a subscriber identification module 724 (e.g., an SIM card), for example. According to an embodiment, the cellular module 721 may perform at least a portion of functions that the processor 710 provides. According to an embodiment, the cellular module 721 may include a communication processor (CP).

Each of the Wi-Fi® module 723, the BT module 725, the GNSS module 727, and the NFC module 728 may include a processor for processing data exchanged through a corresponding module, for example. According to an embodiment, at least a portion (e.g., two or more components) of the cellular module 721, the Wi-Fi® module 723, the BT module 725, the GNSS module 727, and the NFC module 728 may be included within one integrated circuit (IC) or an IC package.

The RF module 729 may transmit and receive a communication signal (e.g., an RF signal). The RF module 729 may include a transceiver, a power amplifier module (PAM), a frequency filter, a low noise amplifier (LNA), an antenna, or the like. According to another embodiment, at least one of the cellular module 721, the Wi-Fi® module 723, the BT module 725, the GNSS module 727, or the NFC module 728 may transmit and receive an RF signal through a separate RF module.

The subscriber identification module (SIM) 724 may include, for example, a card and/or embedded SIM including a subscriber identification module and may include unique identify information (e.g., integrated circuit card identifier (ICCID)) or subscriber information (e.g., integrated mobile subscriber identity (IMSI)).

The memory 730 (e.g., a memory 130) may include an internal memory 732 or an external memory 734. For example, the internal memory 732 may include at least one of a volatile memory (e.g., a dynamic random access memory (DRAM), a static RAM (SRAM), or a synchronous DRAM (SDRAM)), a nonvolatile memory (e.g., a one-time programmable read only memory (OTPROM), a programmable ROM (PROM), an erasable and programmable ROM (EPROM), an electrically erasable and programmable ROM (EEPROM)), a mask ROM, a flash ROM, a flash memory (e.g., a NAND flash memory or a NOR flash memory), a hard drive, or a solid state drive (SSD).

The external memory 734 may include a flash drive, for example, compact flash (CF), secure digital (SD), micro secure digital (Micro-SD), mini secure digital (Mini-SD), extreme digital (xD), multimedia card (MMC), a memory stick, or the like. The external memory 734 may be functionally and/or physically connected to the electronic device 701 through various interfaces.

The sensor module 740 may measure, for example, a physical quantity or may detect an operation state of the electronic device 701. The sensor module 740 may convert the measured or detected information to an electric signal. The sensor module 740 may include at least one of a gesture sensor 740A, a gyro sensor 740B, a pressure sensor 740C, a magnetic sensor 740D, an acceleration sensor 740E, a grip sensor 740F, a proximity sensor 740G, a color sensor 740H (e.g., red, green, blue (RGB) sensor), a biometric sensor 740I, a temperature/humidity sensor 740J, an illuminance sensor 740K, or an ultraviolet (UV) sensor 740M. Although not illustrated, additionally or alternatively, the sensor module 740 may further include, for example, an E-nose sensor, an electromyography sensor (EMG) sensor, an electroencephalogram (EEG) sensor, an electrocardiogram (ECG) sensor, an infrared (IR) sensor, an iris sensor, and/or a fingerprint sensor. The sensor module 740 may further include a control circuit for controlling at least one or more sensors included therein. According to an embodiment, the electronic device 701 may further include a processor which is a part of the processor 710 or independent of the processor 710 and is configured to control the sensor module 740. The processor may control the sensor module 740 while the processor 710 remains at a sleep state.

The input device 750 may include, for example, a touch panel 752, a (digital) pen sensor 754, a key 756, or an ultrasonic input unit 758. The touch panel 752 may use at least one of capacitive, resistive, infrared and ultrasonic detecting methods. Also, the touch panel 752 may further include a control circuit. The touch panel 752 may further include a tactile layer to provide a tactile reaction to a user.

The (digital) pen sensor 754 may be, for example, a part of a touch panel or may include an additional sheet for recognition. The key 756 may include, for example, a physical button, an optical key, a keypad, and the like. The ultrasonic input device 758 may detect (or sense) an ultrasonic signal, which is generated from an input device, through a microphone (e.g., a microphone 788) and may check data corresponding to the detected ultrasonic signal.

The display 760 (e.g., a display 160) may include a panel 762, a hologram device 764, or a projector 766. The panel 762 may be, for example, flexible, transparent, or wearable. The panel 762 and the touch panel 752 may be integrated into a single module. The hologram device 764 may display a stereoscopic image in a space using a light interference phenomenon. The projector 766 may project light onto a screen so as to display an image. The screen may be arranged in the inside or the outside of the electronic device 701. According to an embodiment, the display 760 may further include a control circuit for controlling the panel 762, the hologram device 764, or the projector 766.

The interface 770 may include, for example, an high-definition multimedia interface (HDMI) 772, a universal serial bus (USB) 774, an optical interface 776, or a D-sub (D-subminiature) 778. The interface 770 may be included, for example, in a communication interface 1070 illustrated in FIG. 1. Additionally or alternatively, the interface 770 may include, for example, a mobile high definition link (MHL) interface, a SD card/multi-media card (MMC) interface, or an infrared data association (IrDA) standard interface.

The audio module 780 may convert a sound and an electric signal in dual directions. At least a portion of the audio module 780 may be included, for example, in an input/output interface 150 illustrated in FIG. 1. The audio module 780 may process, for example, sound information that is input or output through a speaker 782, a receiver 784, an earphone 786, or a microphone 788.

The camera module 791 for shooting a still image or a video may include, for example, at least one image sensor (e.g., a front sensor or a rear sensor), a lens, an image signal processor (ISP), or a flash (e.g., an LED or a xenon lamp).

The power management module 795 may manage, for example, power of the electronic device 701. According to an embodiment, a power management integrated circuit (PMIC), a charger IC, or a battery or fuel gauge may be included in the power management module 795. The PMIC may have a wired charging method and/or a wireless charging method. The wireless charging method may include, for example, a magnetic resonance method, a magnetic induction method, or an electromagnetic method and may further include an additional circuit, for example, a coil loop, a resonant circuit, or a rectifier, and the like. The battery gauge may measure, for example, a remaining capacity of the battery 796 and a voltage, current or temperature thereof while the battery is charged. The battery 796 may include, for example, a rechargeable battery or a solar battery.

The indicator 797 may display a specific state of the electronic device 701 or a portion thereof (e.g., a processor 710), such as a booting state, a message state, a charging state, and the like. The motor 798 may convert an electrical signal into a mechanical vibration and may generate the following effects: vibration, haptic, and the like. Although not illustrated, a processing device (e.g., a GPU) for supporting a mobile TV may be included in the electronic device 701. The processing device for supporting a mobile TV may process media data according to the standards of DMB, digital video broadcasting (DVB), MediaFlo®, or the like.

Figure 8:
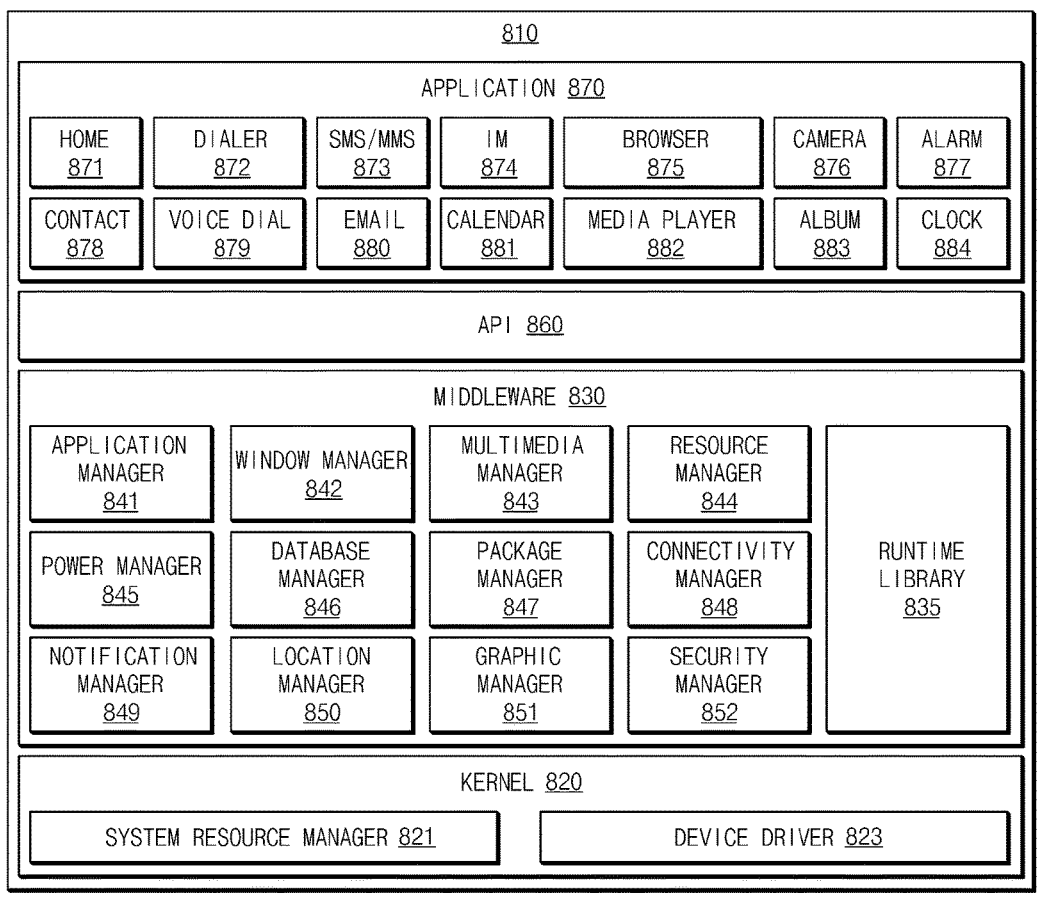
FIG. 8 illustrates a program block according to an embodiment.

FIG. 8 illustrates a program block according to an embodiment.

Referring to FIG. 8, according to various embodiments, a program module 810 (e.g., a program 140) may include an operating system (OS) to control resources associated with an electronic device (e.g., an electronic device 101) and/or diverse applications (e.g., an application program 147) driven on the OS. The OS may be, for example, Android®, iOS®, Windows®, SYMBIAN OS, Tizen®, or Samsung Bada® OS.

The program module 810 may include a kernel 820, a middleware 830, an application programming interface (API) 860, and/or an application 870. At least a part of the program module 810 may be preloaded on an electronic device or may be downloadable from a server 104.

The kernel 820 (e.g., a kernel 141) may include, for example, a system resource manager 831 and/or a device driver 833. The system resource manager 831 may perform control, allocation, or retrieval of system resources. According to an embodiment, the system resource manager 831 may include a process managing part, a memory managing part, or a file system managing part. The device driver 833 may include, for example, a display driver, a camera driver, a Bluetooth driver, a common memory driver, an USB driver, a keypad driver, a Wi-Fi driver, an audio driver, or an inter-process communication (IPC) driver.

The middleware 830 (e.g., a middleware 143) may provide, for example, a function which the application 870 needs in common, or may provide diverse functions to the application 870 through the API 860 to allow the application 870 to efficiently use limited system resources of the electronic device. According to an embodiment, the middleware 830 may include at least one of a runtime library 835, an application manager 841, a window manager 842, a multimedia manager 843, a resource manager 844, a power manager 845, a database manager 846, a package manager 847, a connectivity manager 848, a notification manager 849, a location manager 850, a graphic manager 851, or a security manager 852.

The runtime library 835 may include, for example, a library module which is used by a compiler to add a new function through a programming language while the application 870 is being executed. The runtime library 835 may perform input/output management, memory management, or capacities about arithmetic functions.

The application manager 841 may manage, for example, a life cycle of at least one application of the application 870. The window manager 842 may manage a GUI resource which is used in a screen. The multimedia manager 843 may identify a format necessary for playing diverse media files, and may perform encoding or decoding of media files by using a codec suitable for the format. The resource manager 844 may manage resources such as a storage space, memory, or source code of at least one application of the application 870.

The power manager 845 may operate, for example, with a basic input/output system (BIOS) to manage a battery or power, and may provide power information for an operation of an electronic device. The database manager 846 may generate, search for, or modify database which is to be used in at least one application of the application 870. The package manager 847 may install or update an application which is distributed in the form of package file.

The connectivity manager 848 may manage, for example, wireless connection such as Wi-Fi® or Bluetooth®. The notification manager 849 may display or notify an event such as arrival message, promise, or proximity notification in a mode that does not disturb a user. The location manager 850 may manage location information of an electronic device. The graphic manager 851 may manage a graphic effect that is provided to a user, or manage a user interface relevant thereto. The security manager 852 may provide a general security function necessary for system security or user authentication. According to an embodiment, in the case where an electronic device (e.g., an electronic device 101) includes a telephony function, the middleware 830 may further include a telephony manager for managing a voice or video call function of the electronic device.

The middleware 830 may include a middleware module that combines diverse functions of the above-described components. The middleware 830 may provide a module specialized to each OS kind to provide differentiated functions. Additionally, the middleware 830 may remove a part of the preexisting components, dynamically, or may add a new component thereto.

The API 860 (e.g., an API 145) may be, for example, a set of programming functions and may be provided with a configuration which is variable depending on an OS. For example, in the case where an OS is the android or the iOS, it may be permissible to provide one API set per platform. In the case where an OS is the tizen, it may be permissible to provide two or more API sets per platform.

The application 870 (e.g., an application program 147) may include, for example, one or more applications capable of providing functions for a home 871, a dialer 872, an SMS/MMS 873, an instant message (IM) 874, a browser 875, a camera 876, an alarm 877, a contact 878, a voice dial 879, an e-mail 880, a calendar 881, a media player 882, am album 883, and a timepiece 884, or for offering health care (e.g., measuring an exercise quantity or blood sugar) or environment information (e.g., atmospheric pressure, humidity, or temperature).

According to an embodiment, the application 870 may include an application (hereinafter referred to as "information exchanging application" for descriptive convenience) to support information exchange between the electronic device (e.g., an electronic device 101) and the server 104. The information exchanging application may include, for example, a notification relay application for transmitting specific information to the external electronic device, or a device management application for managing the external electronic device.

For example, the information exchanging application may include a function of transmitting notification information, which arise from other applications (e.g., applications for short message service (SMS)/multimedia messaging service (MMS), e-mail, health care, or environmental information), to an external electronic device. Additionally, the information exchanging application may receive, for example, notification information from an external electronic device and provide the notification information to a user.

The device management application may manage (e.g., install, delete, or update), for example, at least one function (e.g., turn-on/turn-off of an external electronic device itself (or a part of components) or adjustment of brightness (or resolution) of a display) of the external electronic device 102, which communicates with the electronic device, an application running in the external electronic device, or a service (e.g., a call service or a message service) provided from the external electronic device.

According to an embodiment, the application 870 may include an application (e.g., a health care application of mobile medical devices) which is assigned in accordance with an attribute of the external electronic device 102. According to an embodiment, the application 870 may include an application which is received from the server 104 or the external electronic device 102. According to an embodiment, the application 870 may include a preloaded application or a third party application which is downloadable from a server. The component titles of the program module 810 according to the embodiment of the present disclosure may be modifiable depending on kinds of OSs.

According to various embodiments, at least a portion of the program module 810 may be implemented by software, firmware, hardware, or a combination of two or more thereof. At least a portion of the program module 810 may be implemented (e.g., executed), for example, by a processor (e.g., a processor 120). At least a portion of the program module 810 may include, for example, modules, programs, routines, sets of instructions, processes, or the like for performing one or more functions.

Figure 9:
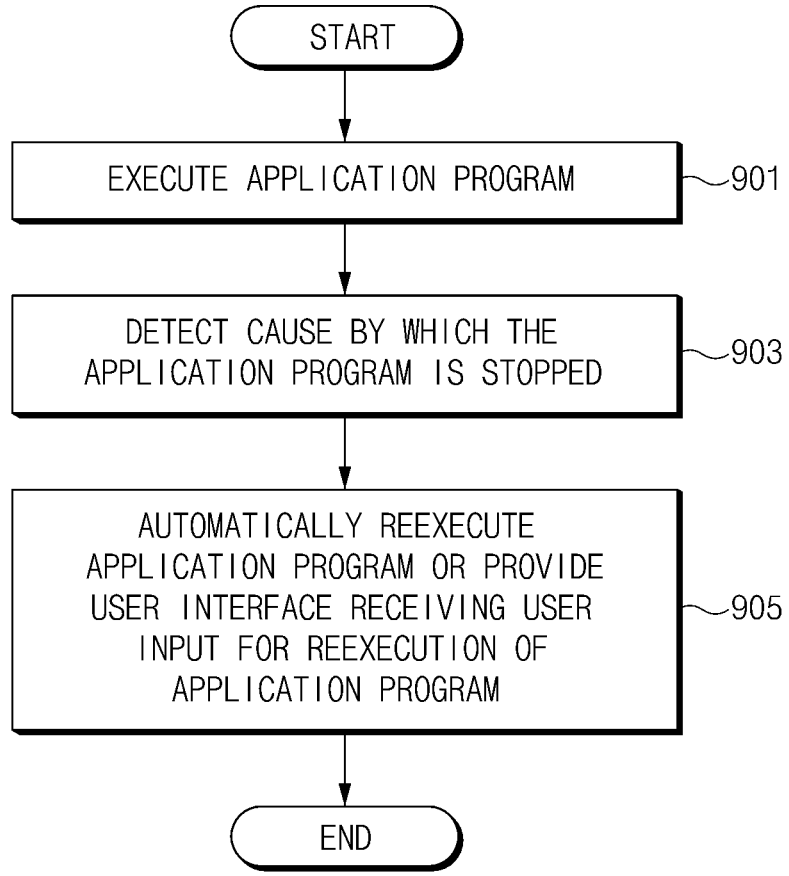
FIG. 9 illustrates a flowchart of a method of operating an application program according to an embodiment.

FIG. 9 illustrates a flowchart of a method of operating an application program according to an embodiment.

Referring to FIG. 9, in association with the operating method of the application program, the electronic device 101 may execute the application program in operation 901. The application program may include at least one of a workout guide application program, a health-related application program, and a muscle making or building related application. The electronic device 101 may provide the icon or menu associated with the at least one application program to execute the application program. Alternatively, the electronic device 100 may execute the specified application program based on predetermined scheduling information when corresponding schedule arrives.

In operation 903, when the application program is stopped, the electronic device 101 may detect a cause by which the application program is stopped. When the application program is not stopped, the electronic device 101 may maintain the execution state of the previous application program.

In operation 905, the electronic device 101 may provide a user interface automatically reexecuting the application program or receiving a user input for the reexecution of the application program on the basis of the detected cause. The user interface may include at least one of a visual user interface (e.g., popup window) or an auditory user interface. The auditory user interface may include, for example, at least one of an output interface outputting specified audio data associated with the user input and an input interface receiving a voice input using a microphone or a gesture input.

In association with the support of the operation of the application program, the electronic device 101 may include a memory storing an application program that provides a guide about a user action and/or collects information on the user action performance and/or a user state and a processor connected to the memory. The memory may store instructions that allow the processor to execute the application program, to detect the cause by which the application program is stopped, and to provide a user interface automatically reexecuting the application program or receiving a user input for the reexecution of the application program on the basis of at least a portion of the detected cause.

Each of the above-mentioned elements of the electronic device according to various embodiments of the present disclosure may be configured with one or more components, and the names of the elements may be changed according to the type of the electronic device. The electronic device according to various embodiments of the present disclosure may include at least one of the above-mentioned elements, and some elements may be omitted or other additional elements may be added. Furthermore, some of the elements of the electronic device according to various embodiments of the present disclosure may be combined with each other so as to form one entity, so that the functions of the elements may be performed in the same manner as before the combination.

The term "module" used herein may represent, for example, a unit including one or more combinations of hardware, software and firmware. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" according to various embodiments of the present disclosure may include at least one of an application-specific IC (ASIC) chip, a field-programmable gate array (FPGA), and a programmable-logic device for performing some operations, which are known or will be developed.

According to various embodiments of the present disclosure, at least a portion of an apparatus (e.g., modules or functions thereof) or a method (e.g., operations) according to various embodiments of the present disclosure, for example, may be implemented by instructions stored in a computer-readable storage media in the form of a programmable module.

A module or a programming module according to an embodiment of the present disclosure may include at least one of the above elements, or a portion of the above elements may be omitted, or additional other elements may be further included. Operations performed by a module, a programming module, or other elements according to an embodiment of the present disclosure may be executed sequentially, in parallel, repeatedly, or in a heuristic method. Also, a portion of operations may be executed in different sequences, omitted, or other operations may be added.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An electronic device comprising:
   a processor; and
   a memory configured to store an application program that performs a workout function in which at least one information on performance of a user action and information on a user state are collected,
   wherein the processor is configured to:
   in response to the application program being stopped while the application program is executed, determine a cause by which the application program is stopped; and
   automatically reexecute the application program or to provide a user interface for receiving a user input for the reexecution of the application program based on the determined cause.

2. The electronic device of claim 1, wherein the application program comprises at least one of a workout guide application program, a health-related application program, or a muscle making or building related application program.

3. The electronic device of claim 1, wherein the user interface comprises at least one of a visual user interface or an auditory user interface.

4. The electronic device of claim 1, wherein the processor is configured to automatically reexecute the application program in a case that the application program is stopped corresponding to a system information generation while the application program is executed.

5. The electronic device of claim 4, wherein the processor is configured to automatically reexecute the application program when the application program is stopped during a generation of at least one of reception of call connection request information from an external electronic device, reception of message information, reception of application execution request information, which is different from the application program, change in background screen, change in theme, or arrival of specified schedule.

6. The electronic device of claim 1, wherein the processor is configured to output information to verify whether the application program is reexecuted when the application program is stopped by receiving user input information associated with an operation of the application program or by a state change occurrence associated with a battery of the electronic device.

7. The electronic device of claim 6, wherein the processor is configured to output information to verify whether the application program is reexecuted in accordance with at least one of reception of input information corresponding to a stop button selection in an execution screen of the application program, reception of input information required to remove the application program in a screen where an application program list is displayed, a battery discharge, a change of a voltage level of the battery to be lower than a predetermined voltage level, or a disconnection of the battery.

8. The electronic device of claim 1, wherein the processor is configured to:
   calculate an estimated workout amount based on first workout information obtained when the application program is stopped and second workout information obtained when the application program is automatically reexecuted or when the application program is reexecuted in accordance with an input; and process the estimated workout amount to a workout amount between a time point at which the application program is stopped and a time point at which the application program is reexecuted.

9. The electronic device of claim 8, wherein the processor is configured to calculate an estimated moving distance based on position information of the first workout information and position information of the second workout information; or calculate an altitude variation of the estimated moving distance based on altitude information of the first workout information and altitude information of the second workout information.

10. The electronic device of claim 1, wherein the processor is configured to output guide information indicating the automatic reexecution of the application program.

11. The electronic device of claim 1, wherein the processor is configured to add a workout record obtained by the reexecution to workout information recorded until the application program is stopped when the application program is reexecuted in response to the user input.

12. A method of operating an application program, comprising:

determining, by an electronic device, a stop of the application program that performs a workout function in which at least one of information on a performance of a user action and information on a user state are collected while the application program is being executed;

detecting, by the electronic device, a cause by which the application program is stopped; and processing, by the electronic device, to automatically reexecute the application program or to provide a user interface for receiving a user input for the reexecution of a application program base on the detected cause.

13. The method of claim 12, wherein the processing comprises automatically reexecuting the application program in a case that the application program is stopped corresponding to a system information generation while the application program is executed or in a case that the application program is stopped during a generation of at least one of reception of call connection request information from an external electronic device, reception of message information, reception of application execution request information, which is different from the application program, change in background screen, change in theme, or arrival of specified schedule.

14. The method of claim 12, wherein the processing comprises outputting information to verify whether the application program is reexecuted in accordance with the stop of the application program by receiving user input information associated with an operation of the application program, by a state change occurrence associated with a battery of the electronic device, or by at least one of reception of input information corresponding to a stop button selection in an execution screen of the application program, reception of input information required to remove the application program in a screen where an application program list is displayed, a battery discharge, a change of a voltage level of the battery to be lower than a predetermined voltage level, or a disconnection of the battery.

15. The method of claim 12, further comprising:

calculating an estimated workout amount based on first workout information obtained when the application program is stopped and second workout information obtained when the application program is automatically reexecuted; and processing the estimated workout amount to a workout amount between a time point at which the application program is stopped and a time point at which the application program is reexecuted.

16. The method of claim 15, wherein the calculating of the workout amount comprises at least one operation of calculating an estimated moving distance based on position information of the first workout information and position information of the second workout information or calculating an altitude variation of the estimated moving distance based on altitude information of the first workout information and altitude information of the second workout information.

17. The method of claim 12, further comprising outputting guide information indicating the automatic reexecution of the application program.

18. The method of claim 12, further comprising adding a workout record obtained by the reexecution to workout information recorded until the application program is stopped when the application program is reexecuted in response to the user input.

19. The method of claim 12, wherein the application program comprises at least one of a workout guide application program, a health-related application program, or a muscle making or building related application.

20. The method of claim 12, wherein the user interface comprises at least one of a visual user interface or an auditory user interface.

* * * * *